(12) United States Patent
Sisken et al.

(10) Patent No.: US 7,572,289 B2
(45) Date of Patent: Aug. 11, 2009

(54) ANCHORING BARB FOR ATTACHMENT TO A MEDICAL PROSTHESIS

(75) Inventors: Richard B. Sisken, West Lafayette, IN (US); Brian D. Choules, Washington, UT (US); Benjamin Nickless, Bloomington, IN (US); Charles W. Agnew, West Lafayette, IN (US)

(73) Assignees: MED Institute, Inc., West Lafayette, IN (US); Cook Incorporated, Bloomington, IN (US)

( * ) Notice: Subject to any disclaimer, the term of this patent is extended or adjusted under 35 U.S.C. 154(b) by 383 days.

(21) Appl. No.: 11/044,522

(22) Filed: Jan. 27, 2005

(65) Prior Publication Data

US 2005/0240259 A1    Oct. 27, 2005

Related U.S. Application Data

(60) Provisional application No. 60/539,391, filed on Jan. 27, 2004.

(51) Int. Cl.
*A61F 2/06* (2006.01)
(52) U.S. Cl. .................... 623/1.36; 623/1.15
(58) Field of Classification Search ................ 623/1.12, 623/1.14, 1.36, 15, 2.36, 2.37; *A61F 2/06*
See application file for complete search history.

(56) References Cited

U.S. PATENT DOCUMENTS

| | | | |
|---|---|---|---|
| 5,375,612 A * | 12/1994 | Cottenceau et al. ......... 128/899 |
| 5,489,295 A | 2/1996 | Piplani et al. |
| 5,693,084 A | 12/1997 | Chuter |
| 5,720,776 A | 2/1998 | Chuter et al. |
| 5,800,526 A | 9/1998 | Anderson et al. |
| 5,863,164 A | 1/1999 | Leistner |
| 5,961,546 A | 10/1999 | Robinson et al. |
| 6,113,612 A | 9/2000 | Swanson et al. |
| 6,200,336 B1 | 3/2001 | Pavcnik et al. |
| 6,221,102 B1 | 4/2001 | Baker et al. |
| 6,231,581 B1 * | 5/2001 | Shank et al. ................. 606/157 |
| 6,506,190 B1 | 1/2003 | Walshe |
| 6,517,574 B1 | 2/2003 | Chuter |
| 6,676,698 B2 | 1/2004 | McGuckin, Jr. et al. |
| 6,849,087 B1 | 2/2005 | Chuter |
| 2003/0120331 A1 * | 6/2003 | Chobotov et al. .......... 623/1.13 |
| 2003/0236570 A1 * | 12/2003 | Cook et al. ................. 623/1.36 |
| 2004/0117004 A1 | 6/2004 | Osborne et al. |
| 2005/0038497 A1 * | 2/2005 | Neuendorf et al. ......... 623/1.15 |

FOREIGN PATENT DOCUMENTS

| | | |
|---|---|---|
| WO | WO 00/35352 | 6/2000 |
| WO | WO 01/76509 A1 | 10/2001 |

* cited by examiner

*Primary Examiner*—Corrine M McDermott
*Assistant Examiner*—Jason-Dennis Stewart
(74) *Attorney, Agent, or Firm*—Brinks Hofer Gilson & Lione

(57) ABSTRACT

A medical prosthesis for implantation within the body of a patient comprises a support structure and an anchoring element that comprises a basal portion and at least one barb extending from the basal portion. The anchoring element may be slidably attached to the strut and the strut may include a first stop and a second stop that define a longitudinal zone of movement for the anchoring element. Other devices and methods are described.

12 Claims, 10 Drawing Sheets

ANCHORING BARB FOR ATTACHMENT TO A MEDICAL PROSTHESIS

CROSS-REFERENCE TO RELATED APPLICATIONS

This application claims priority of provisional application Ser. No. 60/539,391, filed Jan. 27, 2004.

TECHNICAL FIELD

This invention relates to medical devices, more particularly to intraluminal prostheses such as stents, valves, and the like.

BACKGROUND OF THE INVENTION

Prosthetic devices that are delivered intraluminally, such as stents, valves, occluders, shunts, etc., are typically designed to be self expanding or balloon expandable such that they engage the walls of the vessel or duct to become permanently anchored there. To ensure that the prosthesis does not migrate after placement, anchoring barbs are often used that are configured to embed into adjacent tissue and hold the device in place. Barbs are an especially important component of endovascular stent grafts used to exclude an aneurysm sac formed in a blood vessel. For example, the high velocity of blood within the aorta makes it essential to securely anchor the prosthesis when treating an aortic abdominal aneurysm (AAA). Migration of the device downstream can result in the proximal seal of the aneursym sac being compromised, which could be catastrophic in the event that the aneurysm sac ruptures. Barb fixation is method of fixation found in a variety of intraluminal prostheses, such as the ZENITH® Endovascular Stent Graft (Cook Incorporated), which relies on barb to anchor the proximal end of the device in the healthy portion of the aorta above the renal arteries.

In an intraluminal prosthesis formed from a wire frame or support structure, the barbs typically comprise separate elements attached to the frame at strategic points therealong by some method of attachment. Typically, short sections of wire or similar material are used which are soldered to a strut of the frame such that they extend outward for engaging tissue. In the body, solder is subject to corrosion when in contact with bodily fluids, so mechanical methods of attachment have been used as an additional measure to reduce the incidence of barb failure. U.S. Pat. No. 6,200,336 to Pavcnik discloses the use of short section of cannula to further secure the barb to the strut. U.S. Pat. No. 5,720,776 to Chuter et al. discloses the use of a helical coil at the base of the barb that encircles the strut to provide a mechanical attachment in addition to the solder bond. While standard methods such as these usually provide adequate fixation, barb failure due to fracture of the strut or weld is a relatively common phenomenon in situations where there are high repetitive mechanical stresses, often due in part to limitations of the barb design and the method of manufacture and/or attachment.

What is needed is a simplified barb design that is easy to manufacture, is readily and securely attachable to the prosthesis, and that produces predictable results with respect to fatigue life and anchoring ability to maintain the prosthesis at the site of deployment.

SUMMARY OF THE INVENTION

The foregoing problems are solved and a technical advance is achieved in an illustrative medical prosthesis configured for implantation within a bodily lumen that comprises a support structure having a plurality of struts and one or more anchoring elements each formed out of a thin layer of material, such as a thin-wall metal cannula or sheet of metal (e.g., stainless steel or nitinol), wherein a barb is formed from the layer of material that extends out from the basal portion of the anchoring element that is disposed over or around the strut such that the barb is configured to penetrate the tissue of a luminal surface when the prosthesis is implanted in a vessel, duct, organ, or other bodily lumen. By laser-cutting, etching, machining, stamping, otherwise cutting or forming the anchoring element from a cannula or flat sheet of material, additional options are provided for attachment of the anchoring element to the strut of the prosthesis which may yield more uniform and consistent results in manufacturing and performance, as well as potentially reducing costs. For example, an anchoring element or barb made of thin-wall cannula or sheet material and which assumes a generally tubular configuration is formed to slide over or wrap around a strut of the prosthesis such that the basal portion provides a location for spot welding or laser welding as an alternative to soldering the barb to the prosthesis. The disadvantages of using solder include corrosion and/or breakage of the solder joint. Additionally, soldering results in heat being dispersed over a large area of the frame, while laser or spot welding can better concentrate the heat to a more precise location, thus limiting its overall affects on the microstructure of the metal.

In another aspect of the invention, the anchoring element comprises a helix configuration formed from cannula or a flat sheet of material. The helix wraps around the strut of the prosthesis and spaces between the windings provide convenient points for laser weld to affix the anchoring element, thus limiting the extent of weld annealing around the basal region of the barb.

In still another aspect of the invention, the anchoring element is slidably disposed on the strut rather than being permanently affixed. The cannula, or anchoring element formed from flat stock is inserted over or around the strut. Stops that are either attached to, incorporated into the strut, or occur as part of the frame design, limit the longitudinal movement of the anchoring element. By allowing the anchoring element comprising the barb to move in response to forces concentrated at a particular anchor point, it will be less likely to cause the barb to fracture and perhaps lead to migration of the prosthesis. Additionally, a slidable barb can be advantageously configured as a deployable barb system where the barb assumes a first configuration not adapted to engage tissue, such as for the delivery or initial placement of the prosthesis, but is then manipulated into a second configuration or orientation to penetrate the adjacent tissue, such as the luminal wall, and anchor the prosthesis. In a first exemplary embodiment of the present invention, the slidable anchoring element which includes a barb generally extending parallel with the strut, is attached to a actuating system, such as a tether, which urges the anchoring element over the strut until it contacts a deflecting element, such as a ramped structure, located on the strut which forces the barb outward into a position that is better able to penetrate tissue. Optionally, the anchoring element is configured to engage structure located on the strut that locks the anchoring element into the second, engageable position. In a second embodiment, the prosthesis can be deployed with the barb oriented away from the tissue surface, whereby the anchoring element and barb are rotated or otherwise urged or moved into position after the prosthesis is deployed at the implantation site such that the barb tip is able to embed into the adjacent tissue and further anchor the device. Actuation of the anchoring element can be done with releasable tethers, sleeves, sheaths or other mechanisms that restrain the barbs in an inward or otherwise non-engaging orientation, whereby the restraint is released to allow the anchoring element and barbs to resiliently rotate or slide to assume a tissue-engaging position. Spiral threads or grooves, or a twisted strut (e.g., preferable with a non-rounded strut profile) can be used to guide the anchoring element from the first non-engaging position to the second, engageable position. Tethers, wires, pushers, or other mechanical structure may be used to urge the anchoring elements and barbs from a non-engaging position (e.g., via rotation or longitudinal movement of the anchoring element) to one that allows the barbs to penetrate and anchor the device once the prosthesis is in position for final deployment.

Optionally, the anchoring element and strut can be configured such that they slidably engage one another in a manner that limits axial rotation of the anchoring element, thereby ensuring that the barb remains in the desired plane for optimum functionality. This can be accomplished by a variety of methods, including conforming the anchoring element over an at least partially squared strut or having the anchoring element and strut engage one another, such as fitting a tab within a longitudinal groove or other structure, which limits the ability of the anchoring element to twist on the strut while still allowing it to slide longitudinally.

BRIEF DESCRIPTION OF THE DRAWING

Embodiments of the present invention will now be described by way of example with reference to the accompanying drawings, in which:

FIGS. 10-11A depict a partially sectioned top view of illustrative embodiments that include structure to restrict rotation of the anchoring element;

DETAILED DESCRIPTION

The present invention, as embodied by FIGS. 1-16, comprises a an intraluminal medical prosthesis 10 that includes an anchoring element 11 having a barb 12 adapted for penetrating tissue to prevent migration of the prosthesis, the anchoring element 11 being formed from a thin layer of material 14, such as a portion of metal cannula 16 or flat sheet of metal 28 (e.g., stainless steel or nitinol) or other suitable material and configured such that the anchoring element 11 at least partially surrounds or encloses at least one strut 13 of the framework of the prosthesis 10, whereby the anchoring element 11 is either fixedly or slidably secured to a strut or elongate member 13 of the support structure or frame of the prosthesis. The configuration of the strut and prosthesis support structure is not particularly critical to the understanding of the invention. It should also be noted that the term 'cannula', used herein, is defined to encompass both an anchoring element that is originally formed from a piece of existing cannula as well as an anchoring element that is formed from a flat sheet and is shaped into a closed or partially open tubular configuration.

Figure 1:
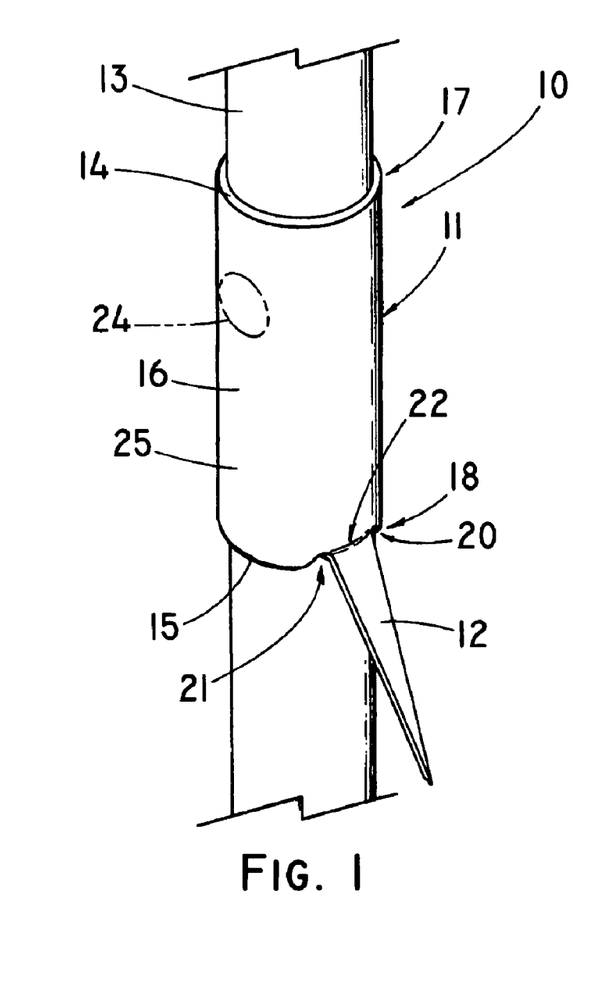
FIG. 1 depicts a perspective view of an illustrative embodiment of the present invention in which the anchoring member comprises a cannula.
Figure 2:
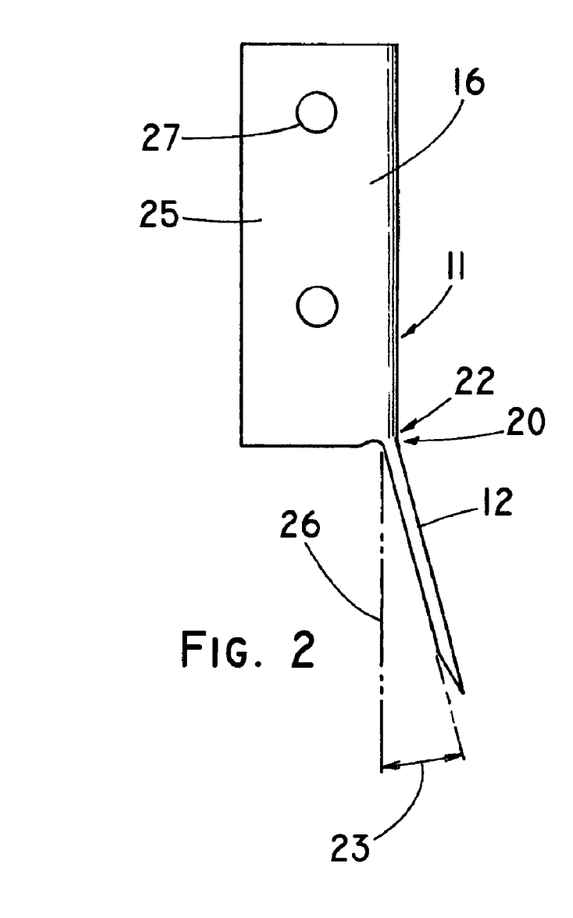
FIG. 2 depicts a side view of an illustrative embodiment having fenestrations located about the basal portion to facilitate welding.
Figure 3:
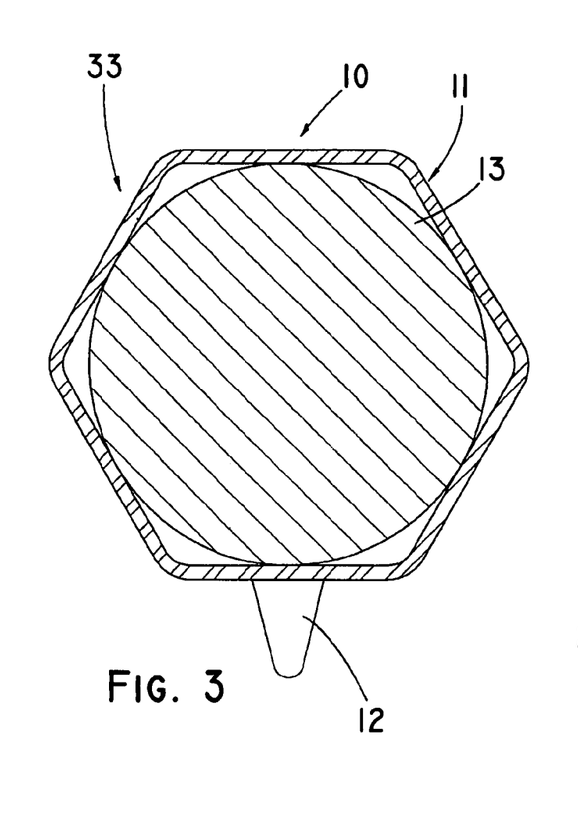
FIG. 3. depicts a partially sectioned top view of an illustrative embodiment in which the anchoring element is crimped to the strut.

FIGS. 1-3 depict an embodiment of the present invention in which the anchoring element 11 is laser cut, machined or otherwise formed out of a piece of cannula, such as 304 stainless steel cannula (e.g., 0.006-0.012" wall), the preferred size and material of the cannula being determined by the dimensions of the strut to which it is attached and the medical application. As depicted in FIG. 1, the anchoring element includes an elongate barb 12 extending from the integral basal portion that extends around the strut. The basal portion 25, that generally tubular portion of the anchoring element 11 that excludes the barb and generally contacts the strut, includes one or more fixation points 14, such as a spot weld, laser weld, crimp, adhesive bond, or other joining mechanism for attaching the anchoring element 11 to the strut 13 or framework of the prosthesis. Fenestrations 27 or open areas formed within the basal portion 25 of the cannula 16, as depicted in FIG. 2, create additional edge areas between the anchoring element 11 and adjacent strut 13 that serve to facilitate laser welding to permanently join the two. Alternatively, or in combination with another method such as welding, crimping may be utilized to help secure the anchoring element 11 to the strut. FIG. 3 depicts a cross-sectional view of an anchoring element 11 that has been crimped over a round wire strut 13 with a crimping tool (not shown) that imparts a hexagonal cross-sectional shape to the cannula, a configuration 33 generally regarded as optimal for creating a secure attachment therebetween.

Referring again to FIGS. 1-2, the barb 12 is typically, but not necessarily, plastically deformed or otherwise set into an angled configuration such that it is better able to penetrate and anchor into tissue when the prosthesis expands to contact the inside of a luminal surface. FIG. 2 depicts the barb 12 set at an angle 23 with respect to the longitudinal axis 26 of the basal portion 25 of the anchoring element 11 (and therefore, the strut 13). When the barb 12 includes a bend 22 about the basal portion 20 thereof, it is usually desirable to include fillets 21 at the base 20 to decrease the stress concentrated at that point and reduce the likelihood of fracture. The cross-sectional profile of the barb 12 is also a factor in producing an optimized anchoring element 11 that is resistant to fracture. It may be desirable to electropolish or otherwise modify its shape, particularly along the basal region, to make it stronger and/or more resistant to fracture.

Figure 16:
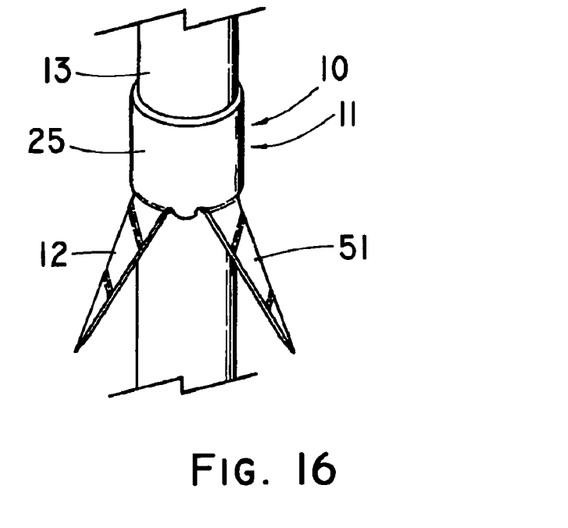

The embodiment of FIG. 16 is similar to that of FIG. 1, except that it includes multiple barbs 12,51 (two in this particular embodiment) that extend from a single basal portion 25 to provide for additional fixation and/or to improve the likelihood that at least one barb is able to adequately penetrate the adjacent luminal surface.

Figure 15:
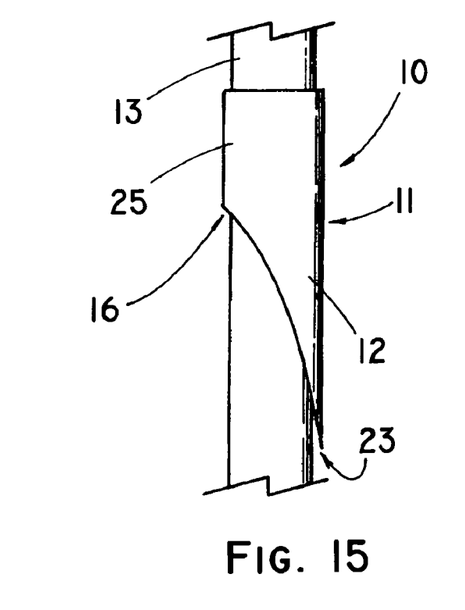

FIG. 15 depicts a similar embodiment formed from a cannula 16 except that the angle 23 of the barb 12 of the anchoring element 11 that angles away from the basal portion 25 is small or negligible to the point that the barb essentially extends parallel with the strut 13. It has been demonstrated in certain devices, such stent grafts to repair aortic aneurysms, a barb 12 having an angle of 10° or less (more preferably 5° or less) with respect to the strut to which it is attached, is able to slowly work itself into adjacent tissue and can provide superior anchoring characteristics over typical angled barbs that are configured to more readily penetrate tissue upon contact. This observation applies to both cannula-based and traditional barb designs.

Figure 13:
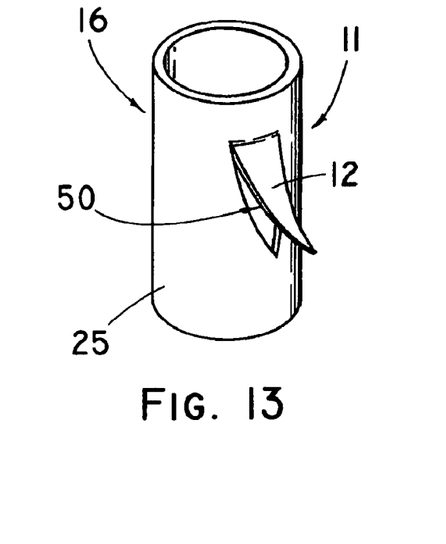
FIGS. 13-16 depict a perspective or side views of various embodiments of anchoring elements formed from a cannula.

FIG. 13 depicts an embodiment in which the anchoring element 11 also comprises a section of cannula 16 in which the barb 12 is created by cutting or forming the outline 50 thereof completely through the cannula wall that comprises the basal portion 25, leaving the base 20 uncut, then deforming the barb 12 outward from the base 20 by an amount to ensure penetration of adjacent tissue.

Figure 14:
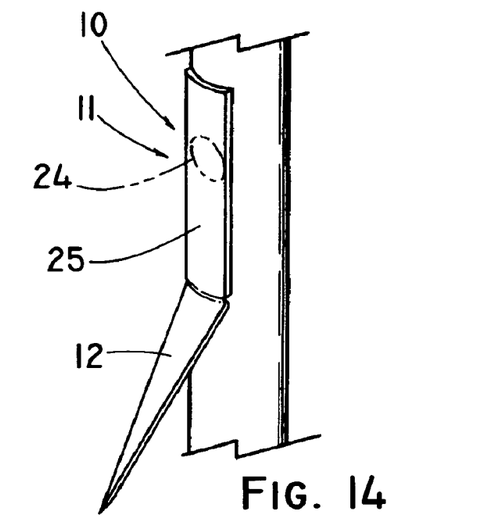

FIG. 14 depicts an embodiment formed from a cannula 16 in which the basal portion 25 is not configured to wrap or extend around a significant portion of the strut, but rather serves merely as a region to locate the weld 24 or otherwise attach the anchoring element 11 to the strut 13.

Figure 5:
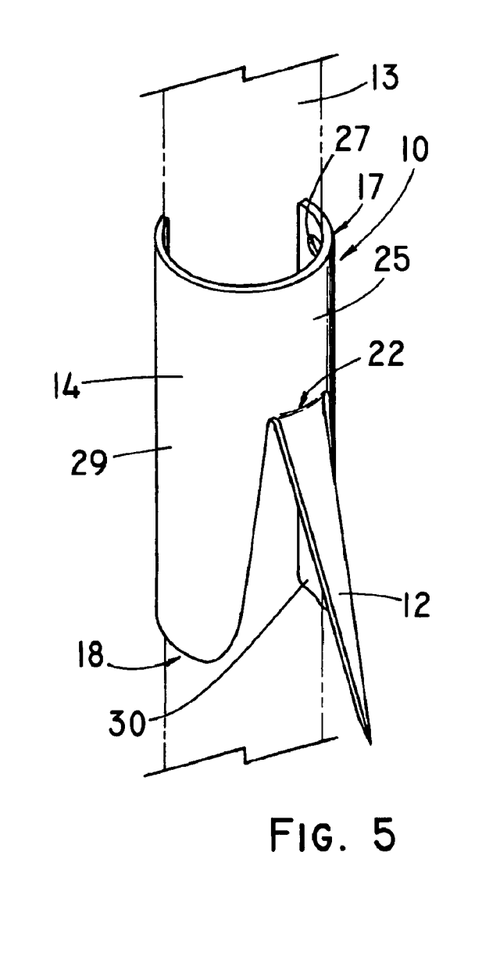
FIG. 5 depicts a perspective view of the embodiment of FIG. 4 that has been formed around and attached to a strut.

One of the primary advantages of forming an anchor or barb from a thin layer of material is that the formation or manufacture of the anchoring element can be accomplished by several well-known methods, including laser cutting, EDM, high-pressure jet, chemical etching, machining, grinding, or stamping, thereby producing or attaching barbs more economically and of more consistent quality than is possible with standard barb fabrication techniques that involve soldering wire barbs to the strut. The technique of stamping barbs 12 would be most appropriate when the source material (thin layer 14) comprises a flat metal sheet 28 or otherwise sheet material suitable for the formation of a barb 12. FIGS. 2-3 depict one embodiment of an anchoring element 11 that is stamped, laser cut, or otherwise formed from a flat sheet 28, then reshaped/deformed to at least partially wrap around or enclose the strut 13 to which it is to be attached, as depicted in FIG. 5. To facilitate attachment, the basal portion 25 can be configured such that it wraps or extends around more than half of the circumference of the strut while leaving an open area or channel at the back to insert the strut thereinto such that the anchoring element is able to 'snap' into place and frictionally engage the strut. The anchoring element can then be further secured to the strut using one of the aforementioned methods.

Figure 4:
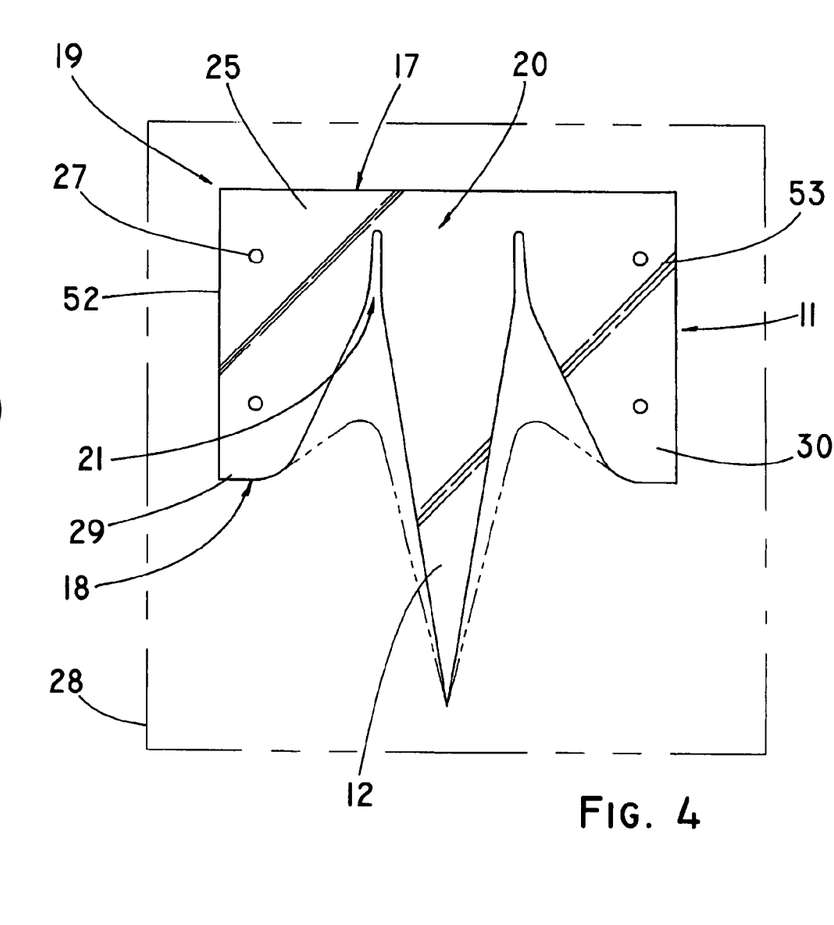
FIG. 4 depicts a top view of an illustrative embodiment formed from a flat sheet of material.
Figure 6:
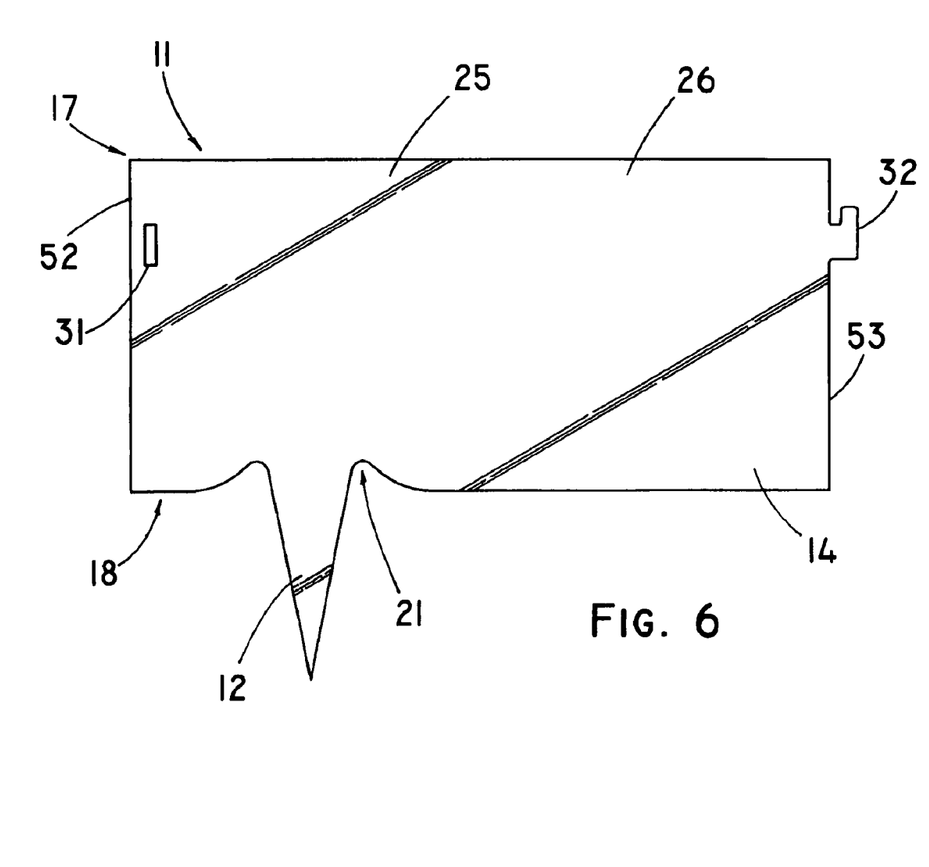
FIG. 6 depicts a top view of an illustrative embodiment that includes a circumferential locking mechanism.

In the illustrative embodiment of FIG. 4, shown in a flat configuration 19 prior to being attached to the support frame, relatively deep fillets provide stress relief to the barb 12, and essentially divide the basal portion 25 into a first 29 and a second 30 portion which include a pair of fenestrations 27 or apertures to facilitate the first and second portions 29,30 being separately attached to the strut. The first and second portions 29,30 may be optionally configured to touch or overlap to be bonded along the seam created between the lateral edges 52,53 thereof as they extend completely around the strut to which they are attached such that the anchoring element 11 generally assumes a tubular configuration. As used herein, the term 'tubular' encompasses a closed cylinder, a partially open cylinder, or a spiral configuration having a generally cylindrical shape. Alternatively, the fillets 21 may be smaller in size (depicted as a broken line) such that the base 20 of the barb is more generally located about the distal end 18 of the basal portion 25 (similar to the cannula embodiment of FIG. 1) rather than the base 20 of the barb being located more proximally within the basal portion 25 (FIG. 4). The depth and configuration of the fillets determines the flexibility of the barb and related properties, such as resistance to fatigue, ability of the barb to penetrate and hold, etc. An embodiment with shallow fillets is depicted in FIG. 6 in which the barb 12 generally extends from the second (distal) end 18 and is located proximate the first lateral edge 52, which also includes a slot 31. The basal portion 25 is configured such that it wraps completely around the strut such that a tab 32 located on the second lateral edge 53 locks into the slot, thereby allowing the anchoring element 11 to enclose the strut 13. Afterward, the anchoring element 11 may be optionally welded, crimped, bonded or otherwise secured to the strut 13. The width of the basal portion 25 depends on the diameter of the strut around which it is attached.

Figure 7:
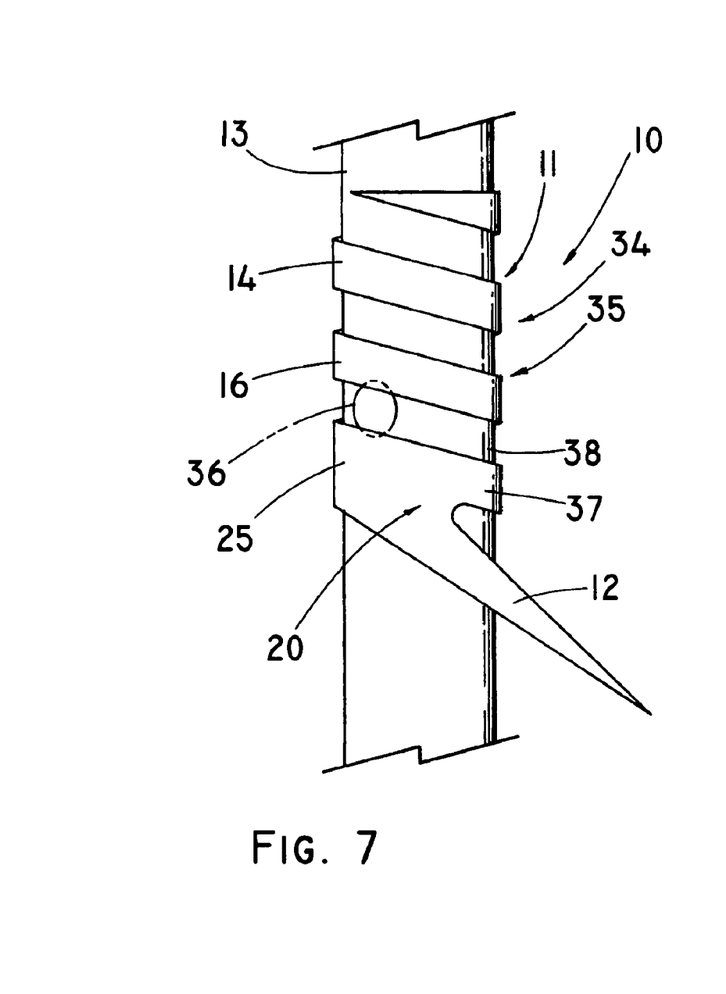
FIG. 7 depicts a side view of an illustrative embodiment comprising a helix configuration.

FIG. 7 depicts a helix-shaped anchoring element 11 that can be formed from either a cannula or a flat sheet 28 which is then plastically deformed or heat-set into that configuration. Unlike the aforementioned cannula anchoring element embodiments, the helix configuration 34 allows it to be wrapped around the strut to which it is attached, especially if made of a highly resilient or shape memory material, rather than requiring it to be inserted over a free end of the strut 13 or support structure and positioned in that manner. Furthermore, the spaces 38 between windings 35 of the basal portion 25 provide edges between anchoring element 11 and strut 13 to facilitate laser welding. The laser welding points 36 are preferably located well proximal of the base 20 of the barb 12, which is attached to the basal winding 37, to prevent the localized annealing of the metal that can weaken the anchoring ability of the barb. By placing the welds between the windings 35 and away from the distal end 18 of the anchoring element 11, less heat is transferred to the critical basal area 20 of the barb 12.

Figure 8:
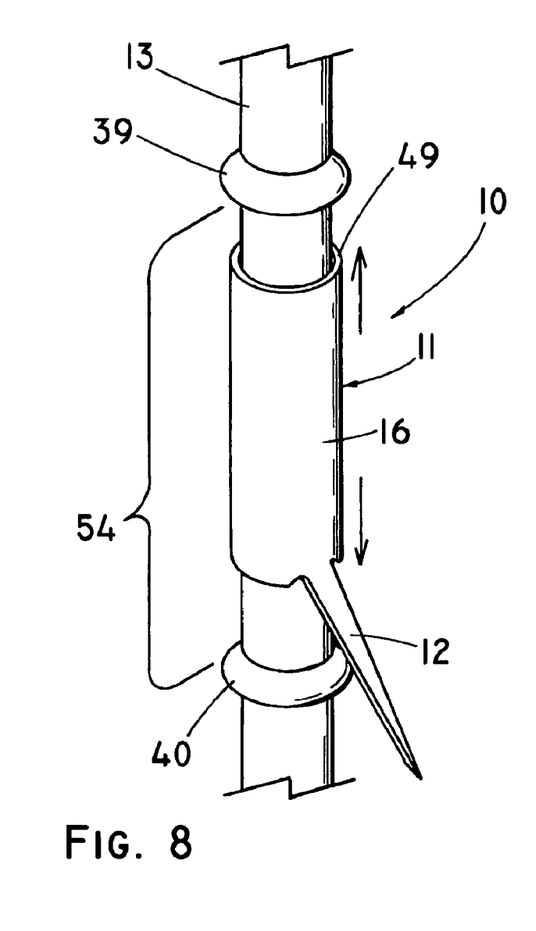
FIG. 8 depicts a perspective view of an illustrative embodiment in which the anchoring element is slidably disposed on the strut.
Figure 9:
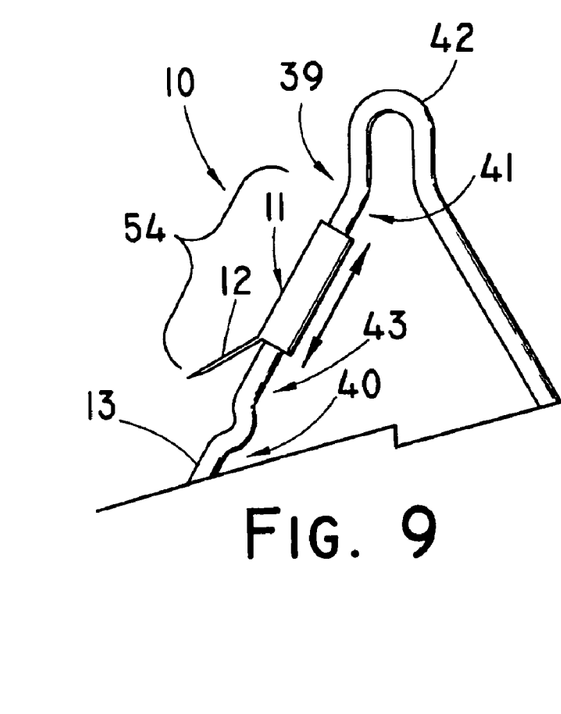
FIG. 9 depicts a side view of an illustrative embodiment in which the longitudinal movement of the anchoring element is limited by bends or kinks within the strut.
Figure 12:
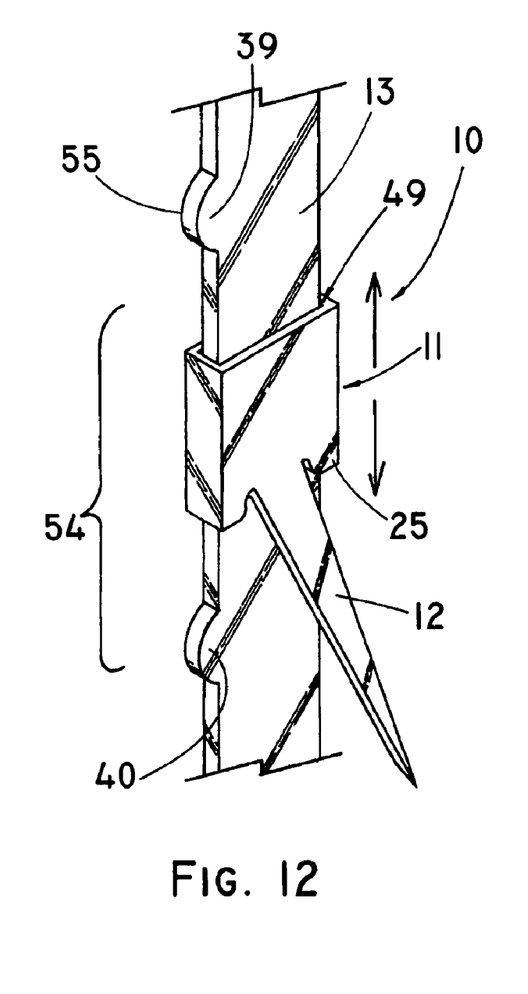
FIG. 12 depicts a perspective view of an illustrative embodiment where a movable barb is attached over a strut formed from a cannula.

As an alternative to fixedly attaching the anchoring element, the anchoring element comprising the barb may be attached such that it is able to move or slide along the strut to better accommodate the load transferred to the barb, while still anchoring the prosthesis at the implantation site. FIG. 8 depicts a cannula-type anchoring element 11 that includes sufficient spacing 49 between the inner surface of strut 13 and the cannula 16 to allow the anchoring element 11 to slide longitudinally along the strut 13. A pair of stops 39,40, such as solder beads, bands, cured adhesive, etc., are attached or applied to the strut. The stops 39,40 limit the longitudinal movement and therefore, define a longitudinal zone 54 of movement for the anchoring element 11. The longitudinal zone 54 of movement has a length greater than that of the anchoring element so that a specific amount of 'play' is selected to allow a barb to move relative to the prosthesis to which it is slidably attached. In addition to the illustrative stops 39,40 depicted in FIG. 8, crimps or kinks 43 and/or bends 41 in the strut, shown respectively as stop 40 and stop 39 in FIG. 9, may be used as well as any structure that limits longitudinal movement of the sliding anchoring element 11. In the embodiment of FIG. 12, in which the struts 13 of the prosthesis support structure are formed (e.g., laser cut) from a cannula, the stops 39,40 are incorporated into the framework pattern as enlarged regions 55 which together establish the longitudinal zone of movement 54 for the anchoring element 11. In alternate bend configurations, the apex 42 of the bend serves as a stop 39 to limit movement of the anchoring element 11.

The embodiment of FIG. 12 comprises an additional useful feature in that the anchoring element 11 can be configured to take advantage of the rectangular or squared profile of the strut to limit the ability of the anchoring element 11 to axially rotate, resulting in sub-optimal or improper orientation of the barb 12 for deployment. By conforming the shape of anchoring element 11 to the strut 13 by wrapping or forming it into a squared-corner shape, the corners or edges of the strut 13 limit the ability of the anchoring element 11 to rotate and thus keep the barb 12 oriented outward within the desired axial plane with sufficient rigidity to penetrate tissue. This also allows the space 49 between the anchoring element 11 and strut 13 to be increased for a 'looser' engagement to better facilitate longitudinal movement of the anchoring element 12, which may be necessary or desirable after the prosthesis 10 has been deployed.

Figure 10:
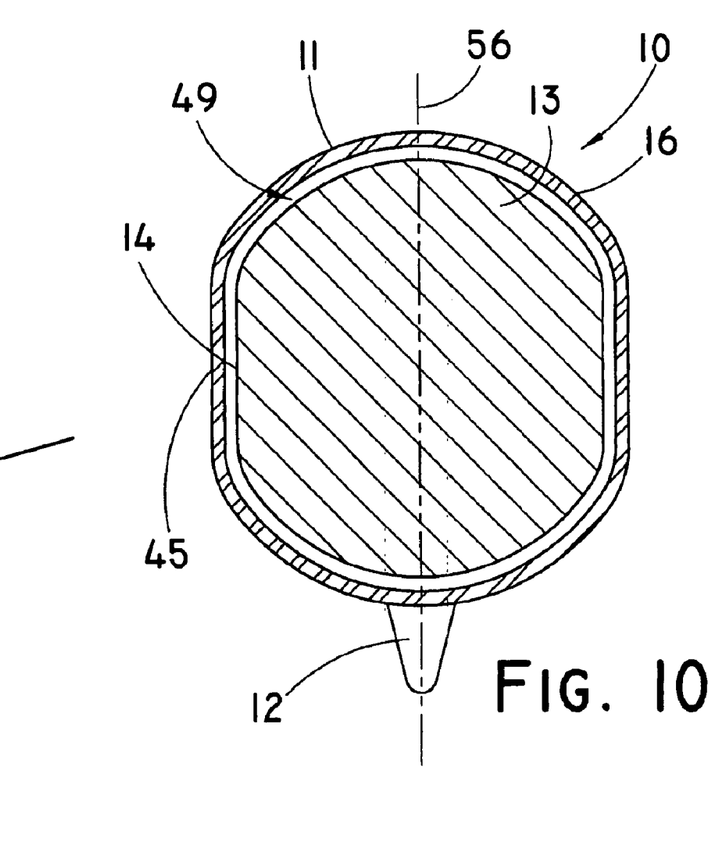

The illustrative embodiment of FIG. 12 depicts one potential solution to the problem of axial rotation of a slidably disposed barb; however, struts 13 formed from rounded wire or otherwise having a circular profile require a somewhat different approach. FIG. 10 depicts an alternative embodiment to limit rotational movement of an anchoring element 11 in which opposite sides of the strut include a flattened area 44 that extends at least along the length of the longitudinal zone 54 that defines the extent of which the anchoring element 11 can travel. The anchoring element 11 includes at least one flattened region 45 corresponding to the flattened area(s) 44 of the strut 13 which limits the ability of the barb 12 to axially rotate out of the predesignated plane 56 optimum for it to perform its intended function.

Figure 11A:
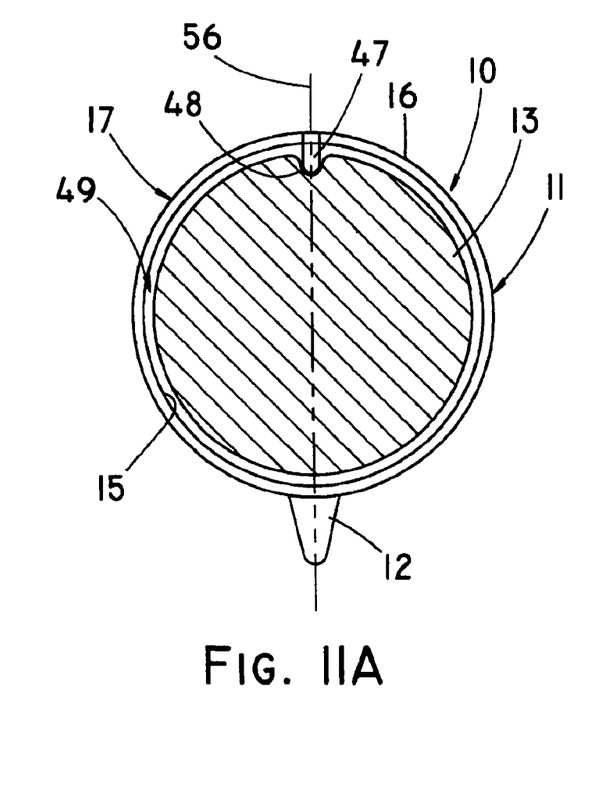
Figure 11B:
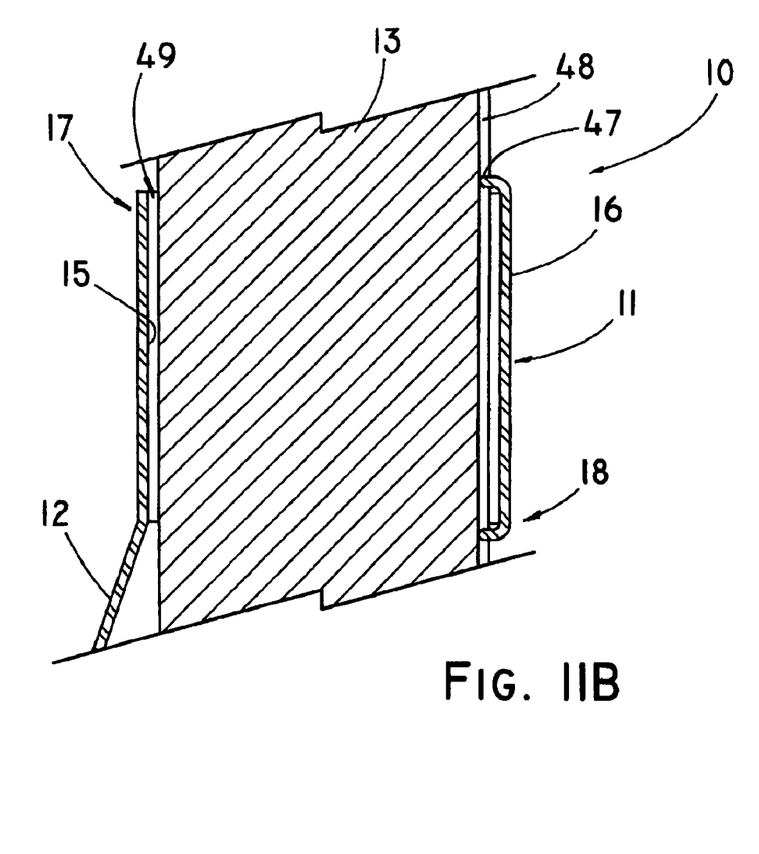
FIG. 11B depicts a lateral cross-sectional view of the embodiment of FIG. 11A.

Another alternative embodiment is depicted in FIGS. 11A-11B in which the anchoring element 11 includes a protuberance or tab 47 that is configured to ride or slide within a groove or channel 48 extending longitudinally along the strut 13. In the illustrative embodiment, the tab 47 is integrally formed along the edge 15 of the proximal end 17 of the basal portion 25 of the anchoring element 11 and angled inward to engage the channel 48 that prevents rotational movement of the anchoring element 11. As depicted in FIG. 11B, tabs 47 may be placed at both the proximal or distal end 17,18 or any suitable location along the basal portion 25 (e.g., only at the distal end 18). One skilled in the art would recognize the existence of numerous other possible structural adaptations that would solve the problem of limiting axial rotation of the anchoring element 11 that is otherwise allowed to slide longitudinally along the strut 13.

Figure 17:
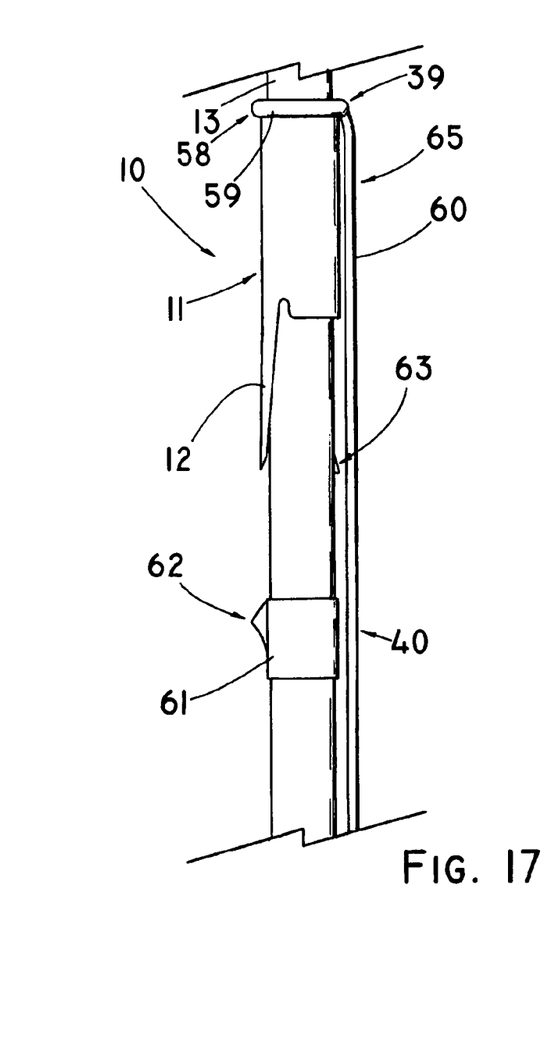
FIG. 17-20 depict side and partially sectioned views of slidable anchoring element embodiments which are deployable from non-tissue engaging position into a configuration for penetrating and anchoring into tissue.

Slidably disposing the barb upon the strut provides the opportunity to configure the anchoring element such that the barb can be manipulated from a first, non-engaging orientation, such as during delivery and the initial deployment procedure, to a second orientation in which the barb can then embed into the adjacent tissue and perform its intended function. FIG. 17 depicts one embodiment of a deployable anchoring element 11 which includes a first position or configuration 65 along the strut in which the barb is oriented downward, generally parallel with the strut, rather than outward in its normal tissue-penetration orientation. This initial orientation 65 advantageously permits the prosthesis 10 to be loaded within a delivery system without having the barbs embedding into the inside surface thereof. Furthermore, the first barb position 65 can allow the prosthesis to be deployed and repositioned at the implantation site, while maintaining control over when the anchoring procedure is initiated to fix final placement. To anchor the prosthesis 10, an actuating mechanism 58 is used to urge the anchoring element 11 along the strut 13 from the first position to a second position or configuration 66 (FIG. 18A) in which the anchoring element contacts a deflecting element 61, which in the illustrative embodiment comprises a band crimped over or otherwise attached to the strut 13. The deflecting element 61 includes a ramped portion 62, whereby as the barb 12 slides over the ramped portion 62, it is deflected outward into the desired angle 23 that allows it to more easily engage and embed into adjacent tissue. The deflecting element 61 functions as the second stop 40 to limit longitudinal movement of the anchoring element 11. Optionally, the anchoring element 11 can be configured with structure (FIG. 18A), such as the illustrative protuberance 63 (e.g., a tab or lip) that is configured to engage compatible structure 67 located along the strut (such as the illustrative recess) that allows the anchoring element 11 to lock in the second position 66 and not slide back proximally toward the first position 65, thereby causing the barb to perhaps become disengaged from the tissue. In the illustrative anchoring element (FIG. 18B), a channel 70 is formed in the inside of the anchoring element 11 cannula in which the protuberance 63 may slide distally until locking into the recess 67. One skilled in the art would appreciate the many alternative engagement mechanisms that would accomplish the same purpose.

Figures 18A, 18B:
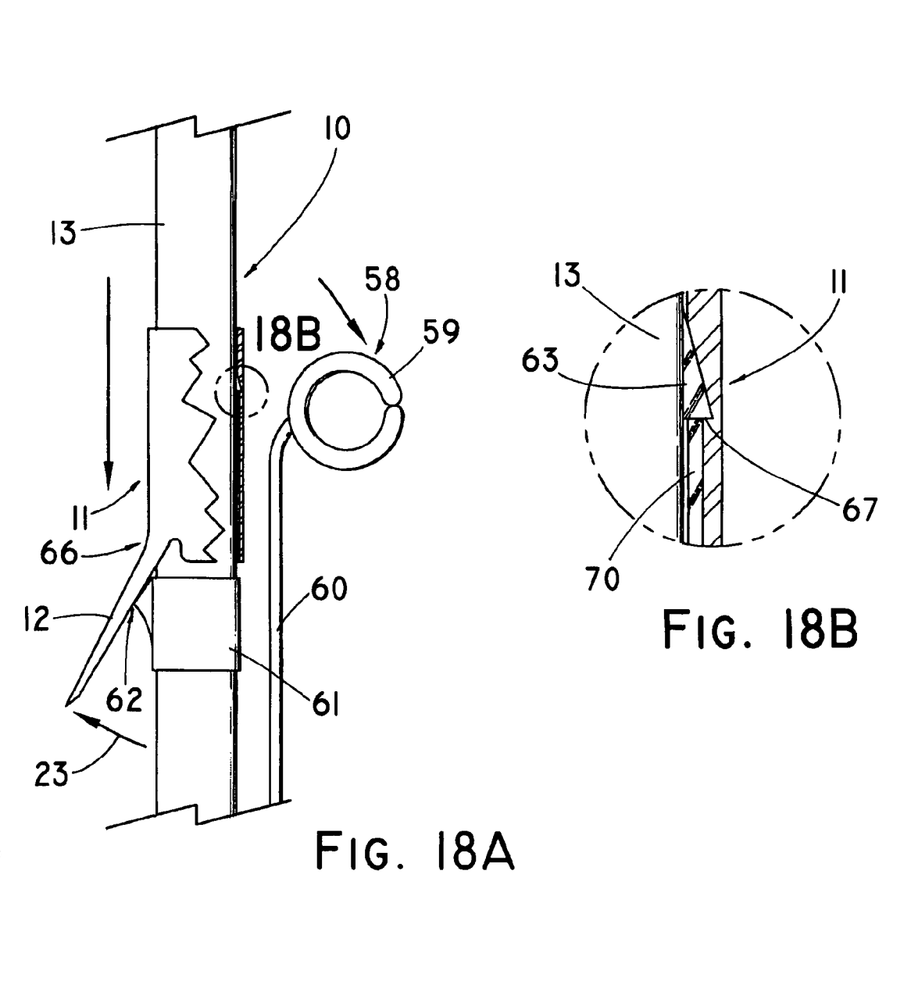

The actuating mechanism 58 of the embodiment of FIG. 18A functions as the first or proximal stop 39 in the embodiment of FIGS. 17-18B, since it limits proximal movement of the anchoring element 11, although alternatively, a separate first stop 39 may be used as well that remains after the actuating mechanism 59 is removed. The illustrative actuating mechanism 58 comprises an urging mechanism, such as the illustrative split ring 59, that is urged distally using a tether 60 that is attached thereto, thereby causing the anchoring element to slide longitudinally toward the second position 66. The tether can be attached to the delivery system or comprise a separate component of the system that is controllable by the operator. When deployment of the barbs 12 is desired, tension is applied to the tether 60 such that when the anchoring element 11 has encountered the resistance provided by the second stop 40, the ring 59 is pulled away from the strut 13 and the entire actuating mechanism removed. Optionally, the tether 60 can be configured to detach from the urging mechanism 59 or the urging mechanism 59 can be configured to break apart or detach in some other suitable manner.

One skilled in the art would appreciate the existence of many potentially suitable solutions to the problem of moving a slidable or rotatable anchoring element from a first position of non-engagement to a second position to facilitate anchoring of the prosthesis.

Figure 19:
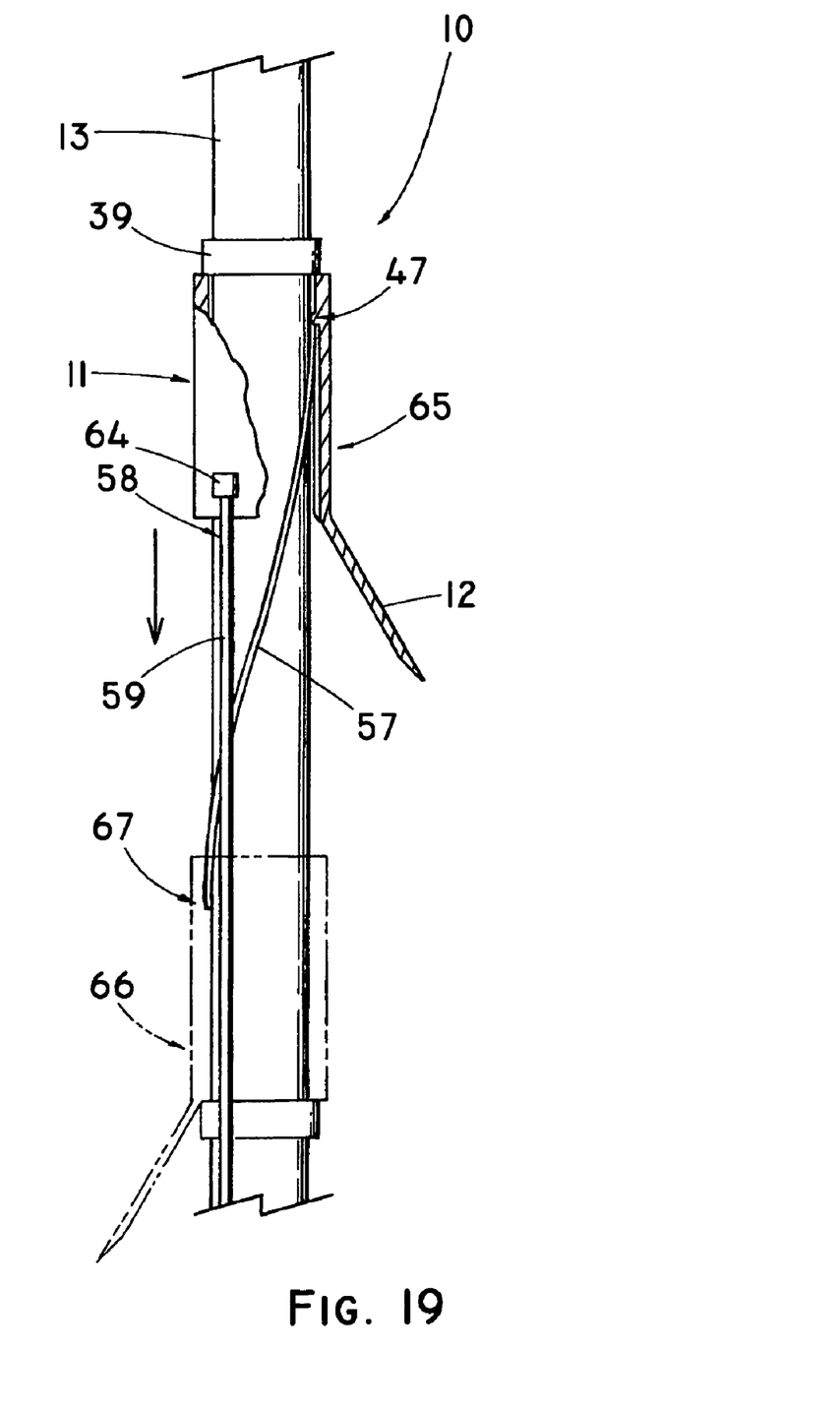
Figure 20:
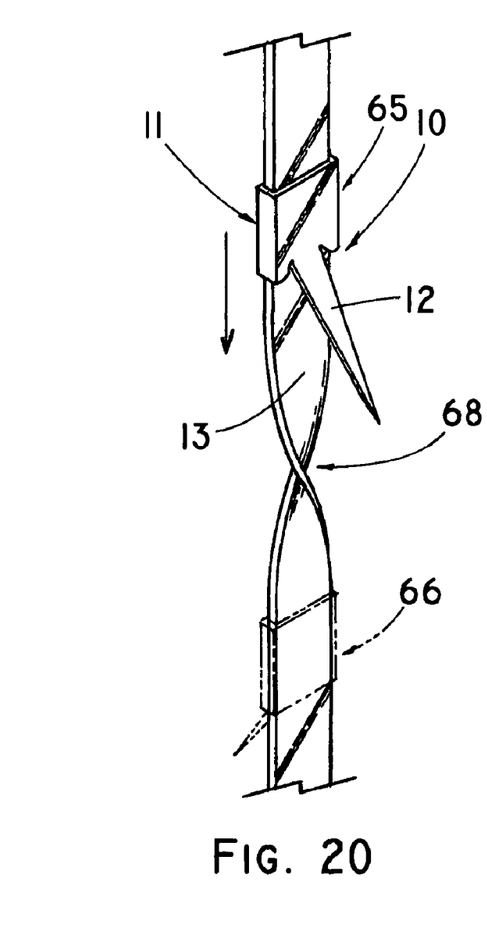

FIGS. 19-20 depict two alternative embodiments in which the anchoring element 11 is rotated from a first position or configuration 65 in which the barb 12 is oriented away from the implantation surface, into a second position or configuration 66 in which the barb 12 is oriented outward into an anchoring position. In the embodiment of FIG. 19 the spiral guide 57 causes the anchoring element 11 to rotate approximately 180° from the first position 65 to the second position 61. The illustrative spiral guide 57 comprises a thread or raised ridge formed on the surface of the strut. One or more guiding protuberances formed along the inner surface of the basal portion 25 of the anchoring element 11 allow the anchoring element 11 to track the spiral ridge 57 which causes the anchoring element 11 and barb 12 to rotate about its axis. Alternatively, the spiral guide can comprise a groove or channel or any combination of raised or recessed structure. To deploy slide the anchoring element 11 along the spiral guide or ridge 57, and an actuating mechanism 59, such as the illustrative elongate member having a releasable connector 64, is attached to the anchoring element 11 and is configured to have sufficient pull force to urge the anchoring element into the deployed configuration 66.

FIG. 20 depicts an embodiment of the present invention in which the strut 13 comprises a twisted configuration 68 (comprising a single twist) that causes the anchoring element 11, when sliding longitudinally in the distal direction (toward the second position 66), to rotate 180° with respect to the strut 13 so that the barb becomes reoriented toward the implantation surface or outer surface of the prosthesis. The squared cross-sectional profile of the illustrative strut allows the anchoring element 11 to track the twisted strut path without other guiding structure being necessary. Alternatively, a rounded, spiral-shaped strut may be used, preferably with the guide structure, such as a groove or ridge, included to facilitate proper orientation of the barb 12.

In another embodiment, the anchoring element can be biased using springs or another well-known mechanism, whereby the bias is released using tethers, sleeves, or other mechanisms to allow the barbs to resiliently rotate or reorient to embed into the adjacent tissue.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in The New Shorter Oxford English Dictionary, 1993 edition. All technical terms shall take on their customary meaning as established by the appropriate technical discipline utilized by those normally skilled in that particular art area. All medical terms shall take their meaning as defined by Stedman's Medical Dictionary, 27$^{th}$ edition.

What is claimed is:

1. A medical prosthesis for implantation within the body of a patient, comprising:
   a support structure comprising at least one strut including a first stop and a second stop;
   an anchoring element comprising a basal portion with at least one barb extending therefrom, wherein the anchoring element is slidably attached to the at least one strut and is slidable along a length of the strut between a first position adjacent the first stop and a second position adjacent the second stop;
   a structure that changes the orientation of the barb when the anchoring element slides from the first position to the second position; and
   an actuation mechanism attached to the barb and a deflecting element located on the strut, wherein the actuating mechanism is operable to urge the anchoring element over the strut until it contacts the deflecting element.

2. A medical prosthesis for implantation within the body of a patient, comprising:
   a support structure comprising at least one strut including a first stop and a second stop;
   an anchoring element comprising a basal portion with at least one barb extending therefrom, wherein the anchoring element is slidably attached to the at least one strut and is slidable along a length of the strut between a first position adjacent the first stop and a second position adjacent the second stop; and
   a structure that changes the orientation of the barb when the anchoring element slides from the first position to the second position;
   wherein the anchoring element is manipulable by rotation and wherein the strut is twisted to guide the anchoring element from the first to the second orientation.

3. A medical prosthesis for implantation within the body of a patient, comprising:
   a support structure comprising at least one strut including a first stop and a second stop;
   an anchoring element comprising a basal portion with at least one barb extending therefrom, wherein the anchoring element is slidably attached to the at least one strut and is slidable along a length of the strut between a first position adjacent the first stop and a second position adjacent the second stop; and
   a structure that changes the orientation of the barb when the anchoring element slides from the first position to the second position;
   wherein the anchoring element is manipulable by rotation and wherein the strut has spiral threads or grooves to guide the anchoring element from the first to the second orientation.

4. A medical prosthesis for implantation within the body of a patient, comprising:
   a support structure comprising at least one strut including a first stop and a second stop;
   an anchoring element comprising a basal portion with at least one barb extending therefrom, wherein the anchoring element is slidably attached to the at least one strut and is slidable along a length of the strut between a first position adjacent the first stop and a second position adjacent the second stop; and
   a structure that changes the orientation of the barb when the anchoring element slides from the first position to the second position;
   wherein the first stop is slidably attached to the strut and is configured to urge the anchoring element towards the second stop.

5. The medical prosthesis of claim 4, wherein the second stop comprises a deflecting mechanism for manipulating the barb between the first and second orientations.

6. The medical prosthesis of claim 5 comprising a lock to lock the barb in the second orientation.

7. A medical prosthesis for implantation within the body of a patient, comprising:
   a support structure comprising at least one strut;
   an anchoring element comprising a basal portion with at feast one barb extending therefrom; and
   an actuation mechanism attached to the barb and a deflecting element located on the strut;
   wherein the at least one barb includes at least one extended configuration for penetrating the tissue of a bodily surface when the prosthesis is implanted thereagainst;

wherein the anchoring element is slidably attached to the at least one strut;

wherein the at least one strut includes a first stop and a second stop, the stops defining a longitudinal zone of movement for the anchoring element, the length of the longitudinal zone being greater than the length of the anchoring element;

wherein the anchoring element is manipulable between a first configuration in which the barb assumes a first orientation and a second configuration in which the barb assumes a second orientation; wherein the second orientation is better adapted for allowing the barb to engage the tissue adjacent the prosthesis than is the first orientation; and wherein the actuating mechanism is operable to urge the anchoring element over the strut until it contacts the deflecting element.

8. A medical prosthesis for implantation within the body of a patient, comprising:

a support structure comprising at least one strut; and an anchoring element comprising a basal portion with at least one barb extending therefrom;

wherein the at least one barb includes at least one extended configuration for penetrating the tissue of a bodily surface when the prosthesis is implanted thereagainst;

wherein the anchoring element is slidably attached to the at least one strut;

wherein the at least one strut includes a first stop and a second stop, the stops defining a longitudinal zone of movement for the anchoring element, the length of the longitudinal zone being greater than the length of the anchoring element;

wherein the anchoring element is manipulable between a first configuration in which the barb assumes a first orientation and a second configuration in which the barb assumes a second orientation; wherein the second orientation is better adapted for allowing the barb to engage the tissue adjacent the prosthesis than is the first orientation; and wherein the anchoring element is manipulable by rotation and the strut is twisted to guide the anchoring element from the first to the second orientation.

9. A medical prosthesis for implantation within the body of a patient, comprising:

a support structure comprising at least one strut; and an anchoring element comprising a basal portion with at least one barb extending therefrom;

wherein the at least one barb includes at least one extended configuration for penetrating the tissue of a bodily surface when the prosthesis is implanted thereagainst;

wherein the anchoring element is slidably attached to the at least one strut;

wherein the at least one strut includes a first stop and a second stop, the stops defining a longitudinal zone of movement for the anchoring element, the length of the longitudinal zone being greater than the length of the anchoring element;

wherein the anchoring element is manipulable between a first configuration in which the barb assumes a first orientation and a second configuration in which the barb assumes a second orientation; wherein the second orientation is better adapted for allowing the barb to engage the tissue adjacent the prosthesis than is the first orientation; and wherein the anchoring element is manipulable by rotation and the strut has spiral threads or grooves to guide the anchoring element from the first to the second orientation.

10. A medical prosthesis for implantation within the body of a patient, comprising:

a support structure comprising at least one strut; and an anchoring element comprising a basal portion with at least one barb extending therefrom;

wherein the at least one barb includes at least one extended configuration for penetrating the tissue of a bodily surface when the prosthesis is implanted thereagainst;

wherein the anchoring element is slidably attached to the at least one strut;

wherein the at least one strut includes a first stop and a second stop, the stops defining a longitudinal zone of movement for the anchoring element, the length of the longitudinal zone being greater than the length of the anchoring element;

wherein the anchoring element is manipulable between a first configuration in which the barb assumes a first orientation and a second configuration in which the barb assumes a second orientation; wherein the second orientation is better adapted for allowing the barb to engage the tissue adjacent the prosthesis than is the first orientation; and wherein the first stop is slidably attached to the strut and is configured to urge the anchoring element towards the second stop.

11. The medical prosthesis of claim 10, wherein the second stop comprises a deflecting mechanism for manipulating the barb between the first and second orientations.

12. The medical prosthesis of claim 11 comprising a lock to lock the barb in the second orientation.

* * * * *

UNITED STATES PATENT AND TRADEMARK OFFICE
CERTIFICATE OF CORRECTION

PATENT NO. : 7,572,289 B2 Page 1 of 1
APPLICATION NO. : 11/044522
DATED : August 11, 2009
INVENTOR(S) : Richard B. Sisken et al

It is certified that error appears in the above-identified patent and that said Letters Patent is hereby corrected as shown below:

In the Claims

In column 10, claim 7, line 62, before "one barb extending" replace "feast" with --least--.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO.        : 7,572,289 B2                                              Page 1 of 1
APPLICATION NO.   : 11/044522
DATED             : August 11, 2009
INVENTOR(S)       : Sisken et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 462 days.

Signed and Sealed this

Seventh Day of September, 2010

David J. Kappos
*Director of the United States Patent and Trademark Office*